United States Patent [19]
Fekete et al.

[11] Patent Number: 5,192,552
[45] Date of Patent: Mar. 9, 1993

[54] PROCESS FOR PREPARING MICROCAPSULES PROVIDING THE RAPID RELEASE OF A DRUG AS ACTIVE INGREDIENT

[75] Inventors: Pál Fekete; Dénes Bezzegh; Katalin Zukovics néSte,uml/u/ megh; Zsuzsanna Jámbor néHoffmann; János Tombor, all of Budapest, Hungary

[73] Assignee: EGIS Gyogyszergyar, Hungary

[21] Appl. No.: 458,600

[22] Filed: Dec. 29, 1989

[30] Foreign Application Priority Data

Dec. 30, 1988 [HU] Hungary ............... 6662/88

[51] Int. Cl.$^5$ ............. A61K 9/50; B01J 13/20; B01J 13/06
[52] U.S. Cl. ............. 424/4.95; 427/213.31; 427/213.36; 428/402.24
[58] Field of Search ........... 427/213.3, 213.32, 213.36, 427/213.31; 424/469, 480, 495

[56] References Cited

U.S. PATENT DOCUMENTS

| | | | |
|---|---|---|---|
| 3,155,590 | 11/1964 | Miller et al. | 424/495 |
| 3,242,051 | 3/1966 | Hiestand et al. | 427/213.3 X |
| 3,341,416 | 9/1967 | Anderson et al. | 424/495 |
| 3,531,418 | 9/1970 | Fanger et al. | 427/213.3 |
| 3,703,576 | 11/1972 | Kitajima et al. | 427/213.3 X |
| 3,951,851 | 4/1976 | Kitajima et al. | 427/213.3 X |
| 4,218,333 | 8/1980 | Samejima et al. | 427/213.3 |
| 4,259,315 | 3/1981 | Lippmann et al. | 424/495 X |
| 4,389,331 | 6/1983 | Samejima et al. | 427/213.3 |
| 4,411,933 | 10/1983 | Samejima et al. | 427/213.3 |
| 4,462,982 | 7/1984 | Samejima et al. | 427/213.3 X |
| 4,540,566 | 9/1985 | Davis et al. | 424/480 |
| 4,540,602 | 9/1985 | Motoyama et al. | 427/213.36 X |
| 4,542,042 | 9/1985 | Samejima et al. | 427/213.3 X |

FOREIGN PATENT DOCUMENTS

| | | | |
|---|---|---|---|
| 157695 | 10/1985 | European Pat. Off. | 424/480 |
| 2332640 | 1/1975 | Fed. Rep. of Germany | 424/495 |
| 22725 | 3/1981 | Japan | 424/480 |
| 8402843 | 8/1984 | PCT Int'l Appl. | 424/480 |

*Primary Examiner*—Robert L. Stoll
*Assistant Examiner*—John M. Covert
*Attorney, Agent, or Firm*—Ostrolenk, Faber, Gerb & Soffen

[57] ABSTRACT

The invention relates to the preparation of microcapsules ensuring direct tablet compression of a drug and rapid release of the drug as active ingredient from the tablets, which comprises microencapsulating the crystal granules of cyclohexane-insoluble active ingredients with a particle size of at most 1000 μm, preferably smaller than 60 μm and particularly preferably smaller than 30 μm, in cyclohexane medium with ethylcellulose taken in an amount of 1:30 to 1:5, preferably 1:20 to 1:10, in relation to the core material, if desired, in the presence of 0.001 to 1.0% by weight/volume, preferably 0.01 to 0.05% by weight/volume, of an anionic surface-active agent; or post-treating the drug granules microencapsulated with ethylcellulose by a cyclohexane-dissolved surface-active agent taken in an amount of 0.001 to 1.0% by weight/volume, preferably 0.1 to 0.5% by weight/volume, in relation to cyclohexane.

17 Claims, No Drawings

PROCESS FOR PREPARING MICROCAPSULES PROVIDING THE RAPID RELEASE OF A DRUG AS ACTIVE INGREDIENT

The invention relates to the preparation of directly tabletable microcapsules providing the rapid release of a drug as active ingredient. More particularly, the invention concerns a process for the preparation of microcapsules ensuring the direct tablet compression of drugs and the rapid release of the drug from the tablets.

The process according to the invention comprises microencapsulating the crystal granules of cyclohexane-insoluble active ingredients with a particle size of at most 1000 μm, preferably smaller than 60 μm and particularly preferably smaller than 30 μm in cyclohexane medium with ethylcellulose taken in an amount of 1:30 to 1:5, preferably 1:20 to 1:10 in relation to the core material, if desired, in the presence of 0.001 to 1.0% by weight/volume (wt/vol) of an anionic surface-active agent; or post-treating the drug granules microencapsulated with ethylcellulose by a cyclohexane-dissolved surface active agent taken in an amount of 0.001 to 1.0% by wt/vol in relation to cyclohexane. Preferably, dialkyl sulfosuccinates and most preferably sodium dioctyl sulfosuccinate are used as anionic surface-active agents.

Microencapsulating processes or microencapsulated products, respectively, are above all used for preparing slow-release (prolonged-release) compositions in the pharmaceutical industry. This is particularly valid for products microencapsulated with ethylcellulose since the release of the drugs from the microcapsules or tablets compressed from the microcapsules is delayed by the water-insoluble microcapsule wall consisting of ethylcellulose. Thus, an overwhelming majority of patent specifications devoted to microencapsulation relates to prolonged-release compositions. The preparation of prolonged-release acetylsalicylic acid microcapsules is published in the U.S. Pat. Nos. 3,341,416, 3,488,418, 3,524,910, 3,703,576, 3,891,570 and 3,951,851; the preparation of prolonged-release indomethacin microcapsules is disclosed in the U.S. Pat. No. 3,557,279.

Processes for the preparation of microcapsules ensuring the slow release of various sorts of drugs by using ethylcellulose as wall substance of the microcapsules are described in other patent specifications. In this processes, the auxiliary agents promoting the possibly complete formation of the ethylcellulose coat, i.e. influencing the so-called phase separation are varied. Processes of such type are published e.g. in the U.S. Pat. Nos. 3,155,590, 3,531,418, 3,909,444, 4,107,072, 4,389,331, 4,411,933 as well as in the published British patent application No. 2,002,318 and in the published European patent applications nos. 38,973 and 99,109.

It is commonly characteristic of the microcapsules prepared by using the above processes that the release of the drug is delayed, 50% of the drug being released during 60 minutes or later. Similarly, the preparation of prolonged-release compositions is published in the Hungarian patent specification No. 187,215, wherein the drug microencapsulated with ethylcellulose is mixed with a limited amount of a water-swellable auxiliary material and compressed to tablets. In this way prolonged-release tablets are prepared which are slowly disintegrated in an aqueous medium.

However, the coating of the crystal granules of drugs with ethylcellulose delays not only the release of the drug but the advantageous compressibility of the coated granules is also ensured by ethylcellulose used as tablet binder. Thus, in the case of microcapsules with a suitable particle size and flowability, the microencapsulated drugs can directly be compressed to tablets without any further granulation. (In the pharmaceutical industry, the process of "direct tablet compression" involves that the drug is mixed with the tablet auxiliary agents, i.e. anti-friction, disintegrating, flowability-promoting and binding agents, and compressed to tablets.) Thus, in these cases the microencapsulation replaces the traditional granulation process which is preferred mainly for drugs which are present in high doses and can be compressed only with difficulties. Namely, in the case of difficulty compressible and high-dose drugs, the use of such a high amount of a binder may eventually be required for achieving a satisfactory tablet compression that this high amount of the binder cannot be dissolved in a utilizable amount of the granulation liquid used in the kneading granulation. On the other hand, when using granulation by fluidization, a volume of granulation liquid is required which makes the time of granulation unrealy long. These problems do not occur during microencapsulation carried out in a cyclohexane suspension and the continuous coat developed on the granule surface is particularly successful for improving to a great extent the tablet compression of drugs with an unfavourable lubrication.

However, the microencapsulation with ethylcellulose, which is extremely simple and widely used for drugs, until now could not be used for the purpose discussed above, actually because of the release-delaying effect of the ethylcellulose coat. Namely, in case of the so-called traditional tablets, the aim is to ensure the most rapid release possible of the drug and the lowest value of release rate of the drug is in every case specified for these compositions in the pharmacopoeias, most widely in USP XXI.

The demand for such utilization of ethylcellulose microcapsules is indicated by the fact that, according to the U.S. Pat. No. 4,123,383 or the equivalent published European patent application No. 76,428, the acceleration of the drug release from the ethylcellulose microcapsules has been tried to be solved by the preparation of microcapsules providing an incomplete coat. According to the process published, the coacervation of ethylcellulose is induced by cooling down the cyclohexane solution of ethylcellulose, then the drug is portionwise added to the thus-formed "empty" microcapsules. By impact of the drug granules and the empty microcapsules maintained in a plastic state, partially coated microcapsules are formed, the coat of which is solidified by cooling down the system. A drawback of this process is that the extent of the "partial" coating can difficulty be regulated and the microencapsulation process is actually not realized because of the partial coating.

Similarly, a process for preparing rapid-release microcapsules is described in U.S. Pat. No. 4,462,982. According to this process, polymeric substances with a small particle size, which are swellable in an aqueous medium, are incorporated to the ethylcellulose microcapsule wall and/or to the core of the microcapsule. A drawback of this process also consists in that the incorporation of water-swellable substances (usually called as disintegrating agents) to the capsule wall requires a very precise control of the microencapsulation process since the incorporation to the wall of these substances becomes possible only after the granules had been coated by ethylcellulose but the coat has not yet been solidified. The incorporation of the disintegrating agents to the microcapsule core actually requires a traditional granulation.

An additional disadvantage of this process is that a relatively large amount of disintegrating agent should be used to achieve the suitably rapid release and therefore, based on the examples, the drug content of the microcapsules can be at most 10 to 65%. In the case of high-dose drugs, the size of the tablet can eventually be increased to an extent making the intake difficult.

Thus, until now one could not develop a process ensuring the rapid release of drugs from microcapsules or tablets compressed from microcapsules in a simple way or by using small amount of other additives.

"Rapid release of the drug" as used hereinafter means the satisfaction of requirements for dissolution prescribed in USP XXI for the traditional tablets, eventually capsules containing a drug as active ingredient.

In the course of our investigations aimed to prepare rapid-release ethylcellulose microcapsules it has unexpectedly been observed that microcapsules, containing a high amount of the drug and ensuring favourable tablet compression as well as rapid release of the drug, can be prepared by carrying out the microencapsulation in the presence of a cyclohexane-soluble anionic surface-active agent or treating the ready microcapsules with the cyclohexane solution of an anionic surface-active agent.

According to the present invention, the ethylcellulose-coated microcapsules are prepared by
  mixing ethylcellulose, the anionic surface-active agent and the drug to be microencapsulated together in cyclohexane at room temperature,
  heating the system to about 80° C. and stirring for 30 to 120 minutes in order to dissolve the ethylcellulose,
  cooling the system down to room temperature (20° to 30° C.) under constant stirring thereby forming a microcapsule suspension,
  removing the microcapsules formed by filtration and drying them.

According to an other embodiment of the process of the invention, the microcapsules can be prepared by
  mixing ethylcellulose with the drug to be microencapsulated in cyclohexane at room temperature,
  heating the system to 80° C. and stirring it for 30 to 120 minutes in order to dissolve the ethylcellulose,
  cooling down the system to room temperature (20° to 30° C.) under constant stirring thereby forming a microcapsule suspension,
  adding an anionic surface-active agent to the microcapsule suspension formed, stirring the system for 30 to 240 minutes, then filtering and drying the microcapsules.

Alternatively, the above first and second embodiments can be combined, i.e. a part of the anionic surface-active agent can be added before the microencapsulation and the other part of it is added after microencapsulation to the system.

The process of the invention can be used for any drug not dissolving in cyclohexane (i.e. when its solubility in cyclohexane at 80° C. is lower than 1%). For a rapid release of the drug, its particle size should be at most 1000 $\mu$m, but suitably its particle size is lower than 60 $\mu$m and most preferably drugs with a particle size below 30 $\mu$m are used.

The ethoxy content of the ethylcellulose used in the process of the invention may be between 48.0 and 49.5%; namely, in case of an other ethoxy content the solubility in cyclohexane of ethylcellulose is too low or too high, respectively, whereby the formation of the microcapsule wall becomes defective or the microcapsules adhere to each other during the filtration or drying. The viscosity of ethylcellulose as measured in 5% concentration solution in a 4:1 toluene/ethanol mixture is 7 to 100 cP, preferably 100 cP. As anionic surface-active agents, tensides dissolving in cyclohexane can only be taken in consideration. From these, the use of dialkyl sulfosuccinates, particularly sodium dioctylsulfosuccinate, is preferred.

It has been found during our investigations that non-ionic surface-active agents or cyclohexane-insoluble anionic surfactants are unsuitable for the use in the process of the invention.

The ratio of ethylcellulose to the core substance can be varied from 1:30 to 1:5, preferably between 1:20 and 1:10. The amount of ethyl cellulose related to cyclohexane is 0.5 to 5% by wt/vol, preferably 2 to 3% by wt/vol.

The amount of the anionic surface-active agent in relation to cyclohexane is 0.001 to 1.0% by wt/vol; in the first process variant, wherein the anionic surface-active agent is added to the system before the microencapsulation, it is 0.01 to 0.05% by wt/vol whereas it is preferably 0.1 to 0.5% by wt/vol when the microcapsules are post-treated. Namely, it has experimentally been shown that, on using the anionic surface-active agent in a concentration above 0.1% by wt/vol in relation to cyclohexane, individual microcapsules of small size are formed the flowability or compressibility, respectively, to tablets of which is not satisfactory. However, this effect was not observed when the microcapsules were post-treated with anionic surface-active agents: in this case, the release of the drug from the microcapsules was accelerated in comparison to the untreated microcapsules.

The role of the anionic surface-active agent in the above process is not quite clear. The molecules of the anionic surface-active agent may be incorporated to the microcapsule wall during the microencapsulation or during the post-treatment of the microcapsules, respectively, and, on the other hand, they can be bound on the surface of the microcapsules through a sorption process. In the first case hydrophilic "channels" can be formed in the inner part of the microcapsule wall whereas in the latter case the outer surface of the microcapsules becomes hydrophilic. Both phenomena lead to a more rapid wetting of the microcapsules and to the acceleration of the drug release.

The mixture useful for tablet compression can be prepared by adding the auxiliary agents (lubricating, disintegrating and gliding agents) commonly used in the tablet production to the microcapsules prepared by using the process according to the invention and then homogenizing the mixture obtained. Filling materials being advantageous for the tablet compression such as microcrystalline cellulose, lactose, etc. can also be employed in case of compositions containing a relatively low amount of the drug.

The invention is illustrated in detail by the aid of the following non-limiting Examples. In order to show the effect of the process according to the invention, the data of release measured on microcapsules prepared in the same way but without anionic surface-active agent are also presented in the Examples for comparison purposes.

EXAMPLE 1

Preparation of microcapsules containing alpha-methyldopa 50 g of alpha-methyldopa, 5 g of tartaric acid (90% by weight of both substances have a particle size below 60 μm) and 5 g of ethylcellulose (STD 100 type, with 48.0 to 49.5% ethoxy content, with a viscosity of 100 cP measured in an Ubbelohde viscosimeter in 5% solution in the mixture of 80% of toluene and 20% of ethanol at 25° C.) are weighed in a three-neck round-bottom flask fitted with a reflux condenser and stirrer. 250 ml of cyclohexane are added and, in the experiments A, B, C, D, E and F, resp., 0.0 g, 0.01 g, 0.025 g, 0.05 g, 0.125 g and 0.5 g, resp., of sodium dioctylsulfosuccinate are added in the same succession. Thus, the concentration of sodium dioctylsulfosuccinate will be 0.0, 0.004, 0.01, 0.02, 0.05 and 0.2% by wt/vol, respectively, in the above succession. The system is heated to 80° C., i.e. to the boiling point of cyclohexane on a water bath under constant stirring and stirring is continued under reflux for one additional hour. Then, the system is allowed to cool down slowly to 50° C. during about one hour and then to 25° C. during additional 30 minutes. The microcapsules formed are recovered by filtration and dried on trays. The particle size of the microcapsules obtained is between 100 and 200 μm in experiments A, B, C and D, and between 20 and 100 μm in experiments E and F (measured by using Alpine air jet sieve). The yield is 93 to 97%.

The microcapsules obtained are homogenized together with the tablet auxiliary agents in a cubiform mixer for 20 minutes and then compressed in an eccentric tablet machine to tablets containing 250 mg of alpha-methyldopa each as active ingredient. In experiments A, B, C and D the substance can well be compressed to tablets: by using a compression pressure of 10,000N, the breaking strength of the tablets of 10 mm in diameter is above 100N whereas in experiment E adhesion and draught can be observed on the compressing devices. No tablets can be prepared in case of experiment F.

The drug release from the tablets was determined in a dissolution-examining rotor equipment according to USP XXI as described in paragraph "Methyldopa Tablets" by using 900 ml of 0.1N hydrochloric acid as dissolving medium under stirring at a rate of 50 rpm. In this case the demand is a dissolution of at least 85% of the drug during 20 minutes (by measuring 6 tablets).

The components of the mixture for tablet compression are as follows:

| | |
|---|---|
| Alpha-methyldopa microcapsules | 50.0 g |
| Colloidal silicon dioxide | 0.24 g |
| Talc | 0.32 g |
| Magnesium stearate | 0.32 g |
| Sodium croscarmellose | 2.72 g |

Results of the dissolution examination:

| Time of dissolution, min. | Dissolved drug % Concentration of sodium dioctylsulfosuccinate % by wt/vol | | | | | |
|---|---|---|---|---|---|---|
| | A 0.0 | B 0.004 | C 0.01 | D 0.02 | E 0.05 | F 0.2 |
| 5 | 37.2 | 32.6 | 74.7 | 81.3 | 100 | It cannot be compressed to tablets . |
| 10 | 47.3 | 43.4 | 85.8 | 97.4 | | |
| 15 | 53.4 | 50.9 | 91.9 | 100 | | |
| 20 | 56.5 | 56.0 | 96.0 | | | |

Thus, based on the above examinations, the release of the drug from the alpha-methyldopa microcapsules reaches the desired extent under effect of sodium dioctylsulfosuccinate taken in an amount of 0.01% by wt/vol calculated for cyclohexane. However, the use of sodium dioctylsulfosuccinate in an amount of 0.05% by wt/vol or more causes a problem in the tablet compression of the microcapsules.

EXAMPLE 2

Post-treatment of alpha-methyldopa microcapsules by sodium dioctylsulfosuccinate The microencapsulation of alpha-methyldopa is performed by using composition A as described in Example 1, i.e. no sodium dioctylsulfosuccinate is used in the microencapsulation; however, after cooling down the microcapsules, 0.025 g of sodium dioctylsulfosuccinate in the experiment G and 0.25 g of sodium dioctylsulfosuccinate in a novel experiment H are weighed to the system at 20° C. After adding the surface-active agent, the system is stirred for one additional hour, then filtered and dried. The microcapsules obtained are compressed to tablets by using the additives and procedure described in Example 1. The drug-release from the tablets was determined as described in Example 1.

Results of the dissolution examinations:

| Time of dissolution, min. | Experiment Concentration of sodium dioctylsulfosuccinate | |
|---|---|---|
| | G 0.01% by wt/vol % | H 0.1% by wt/vol % |
| 5 | 47.7 | 68.9 |
| 10 | 56.3 | 78.6 |
| 15 | 64.9 | 95.5 |
| 20 | 72.6 | 98.4 |

Based on the above results sodium dioctylsulfossucinate, when added afterwards, exerts less effect than it does when used during the microencapsulation (based on the comparison of experiment C to G). The use of sodium dioctylsulfosuccinate in an amount of 0.1% accelerates the dissolution to the extent desired in this case, too, but without any drawback in the tablet compression.

EXAMPLE 3

Example for the comparison of using other surface-active agents

In order to illustrate the unsatisfactory effect of surface-active agents being different from the cyclohexane-soluble anionic surface-active agents used according to the invention, alpha-methyldopa microcapsules are prepared by using two nonionic (Span 60, Brij 78) and an anionic but cyclohexane-insoluble (sodium laurylsulfate) surface-active agents. The microencapsulation is carried out in the experiments I, J and K as described in Example 1 but before the microencapsulation 0.05 g of Span 60 (sorbitan tristearate) or 0.05 g of Brij 78 (polyoxyethylene stearyl ether) or 0.05 g of sodium laurylsulfate, respectively, are added to the system.

The microcapsules obtained are compressed to tablets by using the composition described in Example 1. By determining the drug release from the tablets, the following results were obtained:

| Time of dis- solution, min. | Experiment | | |
|---|---|---|---|
| | I Span 60 % | J Brij 78 % | K Sodium laurylsulfate % |
| 5 | 13.0 | 6.0 | 14.1 |
| 10 | 23.0 | 15.5 | 30.7 |
| 20 | 28.0 | 23.8 | 47.3 |

Based on the above results it can be stated that the drug release is not promoted by using the above surface-active agents.

EXAMPLE 4

Preparation of chloramphenicol microcapsules 50 g of chloramphenicol (90% of the drug have a particle size below 60 μm) and 5 g of ethylcellulose (with a quality as described in Example 1) are weighed in a three-neck round-bottom flask of 500 ml volume fitted with a reflux condenser and stirrer. 250 ml of cyclohexane are added and in experiment I 0.025 g of sodium dioctylsulfosuccinate is added whereas in experiment II the microencapsulation is carried out without adding sodium dioctylsulfosuccinate. In both cases well-filtrable microcapsules are obtained with a particle size of 100 to 200 μm which are compressed to tablets together with the following components:

| Chloramphenicol microcapsules | 50.0 g |
|---|---|
| Colloidal silicon dioxide | 0.36 g |
| Magnesium stearate | 0.45 g |
| Talc | 0.45 g |
| Sodium croscarmellose | 3.27 g |

The above components are homogenized in a cubiform mixer for 20 minutes and then compressed in an eccentric tablet machine to tablets by using a biconvex compressing device of 10 mm in diameter. The breaking strength of the tablets weighing 300 mg each is 70 to 90N.

The drug release from the tablets was determined by using the rotary basket equipment according to USP XXI in 0.1N hydrochloric acid as dissolving medium under stirring at a rate of 100 rpm. In this case the demand is a dissolution higher than 85% during 30 minutes.

Results of the dissolution examinations:

| Time of dissolution, min. | Experiment | |
|---|---|---|
| | I with surface-active agent % | II without surface-active agent % |
| 5 | 41–42 | 27–37 |
| 10 | 63–64 | 44–52 |
| 15 | 79–83 | 53–65 |
| 20 | 91–94 | 63–77 |
| 30 | 100 | 73–87 |

Based on the above results, the drug release to the extent desired is ensured by 0.01% of sodium dioctylsulfosuccinate (calculated for cyclohexane) used during the microencapsulation.

EXAMPLE 5

Preparation of captopril microcapsules

Captopril microcapsules are prepared according to Example 4 in the presence of or without adding sodium dioctylsulfosuccinate (used in an amount of 0.01% by wt/vol). In both cases attractive, white, nearly odourless microcapsules are obtained with a particle size between 100 and 200 μm.

The microcapsules obtained are homogenized together with the following tablet additives for 20 minutes:

| Captopril microcapsules | 27.5 g |
|---|---|
| Microcrystalline cellulose (PH 101) | 10.0 g |
| Hydrogenated castor oil (Cutina H) | 1.0 g |
| Lactose monohydrate | 35.2 g |
| Magnesium stearate | 0.5 g |
| Talc | 0.8 g |
| Formaldehyde-casein (Esma-Spreng) | 5.0 g |

The homogenizate is compressed to tablets of 6 mm in diameter each of which weighs 80 mg and contains 25 mg of the active ingredient. By determining the drug release from the tablets, the following results were obtained:

| Time of dissolution, min. | I With 0.01% by wt/vol of sodium dioctylsulfosuccinate % | II Without surface-active agent % |
|---|---|---|
| 10 | 88.2–92.0 | 85.1–90.4 |
| 20 | 97.4–98.4 | 93.6–97.8 |
| 30 | 98.9–100 | 96.5–100 |

Based on the above results, when the captopril microcapsules are prepared by using ethylcellulose in an amount of 10% by wt/vol (calculated for the drug as active ingredient), a directly compressible product is obtained with an appropriate value of dissolution.

EXAMPLE 6

Preparation of levomepromazine microcapsules

Levomepromazine microcapsules are prepared according to Example 4 in the presence of or without adding sodium dioctylsulfosuccinate in an amount of 0.01% by wt/vol. In both cases an attractive, white product is obtained with a particle size of 100 to 200 μm.

The microcapsules obtained are homogenized together with the following tablet additives for 20 minutes:

| Levomepromazine microcapsules | 37.2 g |
|---|---|
| Microcrystalline cellulose (PH 101) | 8.0 g |
| Colloidal silicon dioxide | 0.6 g |
| Magnesium stearate | 0.7 g |
| Talc | 0.7 g |
| Sodium croscarmellose | 7.2 g |
| Lactose monohydrate (DCL 11) | 25.6 g |
| | 80.0 g |

The homogenizate is compressed to tablets weighing 80 mg and containing 33.8 mg of levomepromazine maleate (25 mg of levomepromazine base) each. By determining the drug release from the tablets, the following results were obtained:

| Time of dissolution, min. | Dissolved drug | |
|---|---|---|
| | I With surface-active agent % | II Without surface-active agent % |
| 5 | 82–83 | 81–85 |
| 10 | 90–93 | 91–93 |
| 15 | 91–95 | 93–97 |

Based on the above results, when the levomepromazine microcapsules are prepared by using ethylcellulose in an amount of 10% by wt/vol (calculated for the drug as active ingredient), a directly compressible product is obtained with a suitable value of dissolution.

EXAMPLE 7

Preparation of meprobamate microcapsules

For the preparation of microcapsules containing meprobamate in the experiments I, II, III and IV, the following components are weighed in the apparatus described in Example 1:

| | I | II | III | IV |
|---|---|---|---|---|
| Meprobamate | 50.0 g | 50.0 g | 50.0 g | 50.0 g |
| Ethylcellulose | 5.0 g | 5.0 g | 7.5 g | 7.5 g |
| Sodium dioctyl-sulfosuccinate | 0.0 g | 0.025 g | 0.0 g | 0.025 g |
| Cyclohexane | 250 ml | 250 ml | 250 ml | 250 ml |

The microencapsulation is performed as described in Example 1. The microcapsules obtained are homogenized with the tablet additives listed hereinafter for 20 minutes. The homogenizate is compressed to tablets of 10 mm in diameter each of which contains 250 mg of the active ingredient.

| Meprobamate microcapsules | 50.0 g |
|---|---|
| Colloidal silicon dioxide | 0.44 g |
| Talc | 0.55 g |
| Magnesium stearate | 0.55 g |
| Sodium croscarmellose | 5.06 g |

The breaking strength of tablets prepared from the microcapsules with compositions I and II is low (2 to 3N) whereas tablets with a suitable strength of 7 to 10N can be compressed from the microcapsules having the compositions III and IV.

EXAMPLE 8

Preparation of paracetamol microcapsules

For the preparation of microcapsules containing paracetamol 50.0 g of paracetamol, 5.0 g of ethylcellulose, 0.025 g of sodium dioctylsulfosuccinate and 250 ml of cyclohexane are weighed in the apparatus described in Example 1. The microencapsulation is carried out as described in Example 1.

The microcapsules are mixed together with the following tablet additives:

| Paracetamol microcapsules | 49.5 g |
|---|---|
| Colloidal silicon dioxide | 0.4 g |
| Magnesium stearate | 0.5 g |
| Talc | 0.4 g |
| Sodium croscarmellose | 2.7 g |

The homogenizate is compressed to tablets containing 600 mg of paracetamol each by using a compressing device of 12 mm.

The following dissolution values were found:

| Time of dissolution, min. | Dissolved drug % |
|---|---|
| 1 | 9–13 |
| 3 | 56–60 |
| 5 | 71–72 |
| 10 | 82–85 |

In this case, the demand of dissolution is at least 80% during 30 minutes. This demand is satisfied by the composition prepared according to the invention.

EXAMPLE 9

Preparation of sulfamethoxazole microcapsules

Microcapsules containing sulfamethoxazole are prepared as described in Example 4 in the presence of or without sodium dioctylsulfosuccinate added in an amount of 0.01% by wt/vol. The microcapsules obtained are mixed together with the following tablet additives:

| Sulfamethoxazole microcapsules | 44.0 g |
|---|---|
| Colloidal silicon dioxide | 0.4 g |
| Magnesium stearate | 0.45 g |
| Talc | 0.45 g |
| Sodium croscarmellose | 4.7 g |

The homogenizate is compressed to tablets of 10 mm in diameter each of which contains 400 mg of active ingredient.

The drug-release from the tablets was determined by using the rotating basket equipment according to USP XXI in 900 ml of 0.1N hydrochloric acid as dissolving medium under stirring at a rate of 100 rpm.

The following dissolution results were obtained:

| Time of dissolution, min. | Dissolved drug | |
|---|---|---|
| | I With surface-active agent % | II Without surface-active agent % |
| 5 | 39–40 | 24–28 |
| 10 | 54–56 | 38–43 |
| 20 | 67–68 | 49–52 |

Thus, the demand of dissolution (i.e. 55% during 20 minute) is satisfied by the tablets compressed from the microcapsules prepared by using surface-active agent.

We claim:

1. A process for preparing ethylcellulose-coated microcapsules, comprising mixing ethylcellulose, a dialkyl sulfosuccinate surface active agent soluble in cyclohexane and a cyclohexane insoluble drug to be microencapsulated together in cyclohexane at room temperature, said drug having a particle size of at most 1000 μm, heating the system to about 80° C. and stirring for 30 to 120 minutes in order to dissolve the ethylcellulose, cooling the system down to room temperature under constant stirring, thereby forming a microcapsule suspension, removing microcapsules formed by filtration and drying them, the proportion of ethyl cellulose to drug being 1:30 to 1:15, and the amount of dialkyl sulfosuccinate surface active agent being 0.001 to 1.0% by weight/volume in relation to the cyclohexane.

2. A process for preparing ethylcellulose-coated microcapsules, comprising mixing ethylcellulose with a cyclohexane-insoluble drug to be microencapsulated in cyclohexane at room temperature, said drug having a particle size of at most 1000 μm, heating the system to about 80° C. and stirring for 30 to 120 minutes in order to dissolve the ethylcellulose, cooling the system down at room temperature under constant stirring, thereby forming a microcapsule, adding a dialkyl sulfosuccinate surface-active agent soluble in cyclohexane to the microcapsule suspension formed, stirring the system for 30 to 240 minutes, then filtering and drying the microcapsules, the proportion of ethyl cellulose to drug being 1:30 to 1:15, and the amount of dialkyl sulfosuccinate surface active agent being 0.001 to 1.0% by weight/volume in relation to the cyclohexane.

3. A process for preparing ethylcellulose-coated microcapsules, comprising mixing ethylcellulose and a cyclohexane insoluble drug to be microencapsulated together in cyclohexane at room temperature, heating the system to about 80° C. and stirring for 30 to 120 minutes in order to dissolve the ethylcellulose, cooling the system down to room temperature under constant stirring, thereby forming a microcapsule suspension, removing microcapsules formed by filtration and drying them, said process further comprising treating the microencapsulated drug or the drug undergoing microencapsulation with a dialkyl sulfosuccinate surface active soluble in cyclohexane prior to removing the microcapsule by filtration.

4. A process as in claim 3, wherein said drug has a particle size of at most 1000 μm, the proportion of ethyl cellulose to drug material is 1:30 to 1:15 and the said dialkyl sulfosuccinate surface active agent is used in an amount of 0.001 to 1.0% by weight/volume in relation to the cyclohexane.

5. A process as in claim 4, wherein said cyclohexane-soluble dialkyl sulfosuccinate surface active agent is sodium dioctylsulfosuccinate.

6. A process as in claim 4, wherein the particle size of said crystal granules is less than 60 μm.

7. A process as in claim 4, wherein the particle size of said crystal granules is less than 30 μm.

8. A process as in claim 4, wherein the proportion of ethylcellulose to the microencapsulated material or the material undergoing microencapsulation is 1:20 to 1:10.

9. A process as in claim 4, wherein the microencapsulated material or the material undergoing microencapsulation is treated with 0.01 to 0.05% weight/volume of said cyclohexane-soluble dialkyl sulfosuccinate surface-active agent.

10. A process as claimed in claim 4, which comprises using L-3-(3,4-dihydroxyphenyl)-2-methylalanine (α-methyldopa) as active ingredient.

11. A process as claimed in claim 4, which comprises using 2,2-dichloro-N-[2-hydroxy-1-hydroxymethyl-2-(4-nitrophenyl)ethyl]acetamide (chloramphenicol) as active ingredient.

12. A process as claimed in claim 4, which comprises using 1-(3-mercapto-2-methyl-1-oxopropyl)-L-proline (captopril) as active ingredient.

13. A process as claimed in claim 4, which comprises using (R)-2-methoxy-N,N,3-trimethyl-10H-phenothiazine-10-propanamine (levomepromazine) as active ingredient.

14. A process as claimed in claim 4, which comprises using 2-methyl-2-n-propyl-1,3-propanediol dicarbamate (meprobamate) as active ingredient.

15. A process as claimed in claim 4, which comprises using N-(4-hydroxyphenyl)acetamide (paracetamol) as active ingredient.

16. A process as claimed in claim 4, which comprises using 4-amino-N-(5-methyl-3-isoxazolyl)benzenesulfonamide (sulfamethoxazole) as active ingredient.

17. A microencapsulated drug produced by the process of claim 3.

* * * * *